United States Patent [19]

Wang et al.

[11] Patent Number: 5,639,594
[45] Date of Patent: Jun. 17, 1997

[54] LINEAR AND BRANCHED PEPTIDES EFFECTIVE IN DIAGNOSING AND DETECTING NON-A, NON-B HEPATITIS

[75] Inventors: Chang Yi Wang, Cold Spring Harbor; Barbara Helen Hosein, Manhattan, both of N.Y.

[73] Assignee: United Biomedical, Inc., Hauppauge, N.Y.

[21] Appl. No.: 83,947

[22] Filed: Jun. 28, 1993

Related U.S. Application Data

[63] Continuation-in-part of Ser. No. 946,054, Sep. 15, 1992, which is a continuation-in-part of Ser. No. 719,819, Jun. 24, 1991, which is a continuation-in-part of Ser. No. 667,275, Mar. 11, 1991, abandoned, which is a continuation-in-part of Ser. No. 651,735, Feb. 7, 1991, abandoned, and Ser. No. 805,374, Dec. 11, 1991, which is a division of Ser. No. 558,799, Jul. 26, 1990, Pat. No. 5,106,726, which is a continuation-in-part of Ser. No. 510,153, Apr. 16, 1990, abandoned, which is a continuation-in-part of Ser. No. 481,348, Feb. 16, 1990, abandoned.

[51] Int. Cl.$^6$ ............... C12Q 1/70; A61K 39/29; C07K 17/02
[52] U.S. Cl. ............ 435/5; 424/228.1; 424/189.1; 530/324
[58] Field of Search ............ 435/5; 530/324; 424/228.1, 189.1

[56] References Cited

U.S. PATENT DOCUMENTS

| | | | |
|---|---|---|---|
| 4,629,783 | 12/1986 | Cosand | 530/324 |
| 5,106,726 | 4/1992 | Wang | 435/5 |
| 5,191,064 | 3/1993 | Arima et al. | 530/324 |
| 5,229,491 | 7/1993 | Habets et al. | 530/326 |

FOREIGN PATENT DOCUMENTS

| | | |
|---|---|---|
| 0318216 | 5/1988 | European Pat. Off. |
| 0468527 | 1/1992 | European Pat. Off. |
| 0529493 | 3/1993 | European Pat. Off. |
| 0531974 | 3/1993 | European Pat. Off. |
| 0586065 | 3/1994 | European Pat. Off. |
| 593290 | 4/1994 | European Pat. Off. |
| 593291 | 4/1994 | European Pat. Off. |
| WO9115516 | 10/1991 | WIPO. |
| WO9222655 | 12/1992 | WIPO. |
| WO9300365 | 1/1993 | WIPO. |
| WO9309253 | 5/1993 | WIPO. |
| WO9325575 | 12/1993 | WIPO. |
| WO9413700 | 6/1994 | WIPO. |

OTHER PUBLICATIONS

Farci, et al. "Lack of protective immunity against . . . ," Science 258:135–140 (1992).
Audibert et al., "Adjuvants: current status, clinical perspectives . . . ," Immunol Today 14:281–284 (1993).

Kuo et al, (1989) Science 244:362–364, An Assay for Circulating Antibodies to a Major Etiologic Virus of Human Non-A, Non-B Hepatitis.

Arima, et al, (1989) Gastroenterologia Japonica 24:540–544 Cloning of a cDNA associated with acute and chronic hepatitis C infection generated from patients serum RNA.

Arima et al, (1989) Gastroenterologica Japonica 24:545–548 A lambda gtll–cDNA clone specific for chronic hepatitis C generated from pooled serum presumably infected by hepatitis C virus.

Maeno et al, (1990) *Nucleic Acid Research* 18:2685–2689 A cDNA clone closely associated with non–A, non–B hepatitis.

Reyes et al, (1990) *Science* 247: 1335–1339 Isolation of cDNA from the Virus Responsible for Enterically Transmitted Non–A, Non–B Hepatitis.

Okamoto et al, (1990) *Japan J. Exp. Med.* 60:167–177 The 5'–Terminal Sequence of the Hepatitis C Virus Genome.

Kato et al, (1990) Proc. Natl. Acad. Sci. 87:9524–9528 Molecular cloning of the human hepatitis C virus genome from Japanese patients with non–A, non–B hepatitis.

Mishiro et al, (1990) Lancet 336:1400–1403 Non–A, Non–B hepatitis specific antibodies directed at host–derived epitope: implication for an autoimmune process.

Hosein et al, (1990) Proc. Natl. Acad. Sci. 88:3647–3651 Improved serodiagnosis of hepatitis C virus infection with synthetic peptide antigen from capsid protein.

Okamoto et al, (1992) *J. Gen. Virology* 73:673–679 Typing hepatitis C virus by polymerase chain reaction with type–specific primers: application to clinical surveys and tracing infectious sources.

*Primary Examiner*—Michael P. Woodward
*Attorney, Agent, or Firm*—Morgan & Finnegan, L.L.

[57] ABSTRACT

The present invention relates to novel linear and branched peptides specific for the diagnosis and prevention of non-A, non-B hepatitis (NANBH), as well as hepatitis C virus (HCV) infection. More particularly, the present invention is directed to linear peptides diagnostic for NS-3 of HCV as well as branched synthetic substituted and hybrid peptides containing at least one epitope which is effective in detecting NANBH-associated antibodies in patients with NANBH using immunoassay techniques. In addition, this invention provides immunoassays for the detection and diagnosis of NANBH using the subject peptides, vaccine compositions for prevention and treatment of NANBH or HCV infection as well as a method of treating or preventing NANBH and HCV infection.

15 Claims, No Drawings

LINEAR AND BRANCHED PEPTIDES EFFECTIVE IN DIAGNOSING AND DETECTING NON-A, NON-B HEPATITIS

This application is a continuation-in-part of U.S. Ser. No. 946,054, filed Sep. 15, 1993, which is a continuation-in-part of U.S. Ser. No. 719,819, filed Jun. 24, 1991, which is a continuation-in-part of U.S. Ser. No. 667,275, filed Mar. 11, 1991, which is a continuation-in-part of U.S. Ser. No. 651,735, filed Feb. 7, 1991, and of U.S. Ser. No. 805,374, filed Dec. 11, 1991, which is a divisional of U.S. Ser. No. 558,799, filed Jul. 26, 1990, now U.S. Pat. No. 5,106,726, which is a continuation-in-part of U.S. Ser. No. 510,153, filed Apr. 16, 1990, abandoned, which is a continuation-in-part of U.S. Ser. No. 481,348, filed Feb. 16, 1990, abandoned.

FIELD OF THE INVENTION

The present invention relates to novel linear and branched peptides specific for the diagnosis and prevention of non-A, non-B hepatitis (NANBH), including hepatitis C virus (HCV) infection. More particularly, the present invention is directed to linear and to branched synthetic peptides containing at least one epitope which is effective in detecting NANBH-associated antibodies in patients with NANBH using immunoassay techniques. Further, the present invention is directed to synthetic peptides which are hybrids of the peptides described herein. In addition the subject peptides can be used as antigens to elicit monoclonal or polyclonal antibodies against HCV and as immunogens in vaccines for prevention and treatment of NANBH or HCV infection.

BACKGROUND OF THE INVENTION

Non-A, non-B hepatitis (NANBH) remains the most common form of post-transfusion hepatitis, imposing a strong need for sensitive and specific diagnostic screening methods to identify potential blood donors and other persons who may be carriers of the disease. Thus, accurate screening methods are needed to permit removal of contaminated blood and blood products from the blood supply with a high degree confidence.

The etiological agent of NANBH, HCV, has been cloned and identified by several groups [Houghton et al., EP 0318216, published 5/1989; Okamoto et al. (1990) *Jpn. J. Exp. Med.* 60:167; Houghton et al., EP 0388232, published 9/1990; and Kato et al. (1990) *Proc. Natl. Acad. Sci. USA* 87:9524; Arima et al. (1989a) *Gastroenterologia Japonica* 24:540; Reyes et al. (1990) *Science* 247:1335; Arima et al. (1989b) *Gastroenterologia Japonica* 24:545; Maeno et al. (1990) *Nucleic Acids Res.* 18:2685]. The HCV genome is about 10 kilobases (kb) in length and encodes a single polyprotein which is processed into structural and non-structural proteins. From the N terminus, the polyprotein includes the capsid and envelope proteins of the structural region and the NS-1 to NS-5 proteins of the non-structural region.

While some antigenic regions of HCV have been identified, peptides and recombinant proteins from these regions exhibit a variable degree of sensitivity and selectivity in detection and diagnosis of NANBH carriers. Antigenic regions have been reported in the core, or capsid, protein [Hosein et al. (1991) *Proc. Natl. Acad. Sci. USA* 88:3647; UBI HCV EIA Product Insert (1990); Okamoto et al. (1990) *Jap. J. Exp. Med.* 60:223; U.S. Pat. No. 5,106,726; Takahashi et al. (1992) *J. Gen. Virol.* 73:667; Kotwal et al. (1992) *Proc. Natl. Acad. Sci. USA* 89:4486]; in the envelope, NS-1, NS-2 and NS-3 proteins [Wang et al., EP 0468527, published Jan. 29, 1992]; NS-4 protein [Houghton (1989); Kuo et al. (1989) *Science* 244:362; U.S. Pat. No. 5,106,726] and NS-5 protein [Maeno et al. (1990) *Nucleic Acids Res.* 18:2685; Wang (1992)].

In addition to HCV-derived antigens, there exist other NANBH-associated antigens that appear to be encoded by a host cellular sequence. One such antigen, known as the GOR epitope, is reactive with sera from individuals who are PCR positive for HCV [Mishiro et al. (1990) *Lancet* 336:1400].

Serological analysis has been used to map epitopes within certain HCV antigenic regions as described in Wang (1992) and U.S. Pat. No. 5,106,726, each of which is incorporated herein by reference. These mapping studies employed synthetic peptides to screen well-characterized NANBH serum panels and permitted identification of highly immunoreactive HCV antigens. Further refinement of the epitope analysis using serological validation techniques has led to the discovery that small clusters of amino acid residues contained within longer peptides or fusions of peptides containing one or more epitopes from separate regions of the HCV genome can provide a superior and more sensitive assay for diagnosis and detection of NANBH carriers as well as for HCV infection. Extensive testing of long, overlapping peptides covering the NS-3 region has led to the identification of a group of immunodominant peptides containing conformational epitopes. This group of peptides is of particular use in detecting NANBH-associated antibodies.

SUMMARY OF THE INVENTION

The present invention relates to linear and to branched synthetic peptides for the diagnosis and detection of NANBH and HCV infection. In particular the subject peptides are provided as a peptide composition having at least one linear peptide or at least one branched peptide.

The linear peptides are specifically immunoreactive with antibodies against HCV and are derived from an amino acid sequence from the group consisting of sequence of Ala-Leu-Ser-Thr-Thr-Gly-Glu-Ile-Pro-Phe-Tyr-Gly-Lys-Ala-Ile-Pro-Leu-Glu-Val-Ile-Lys-Gly-Gly-Arg-His-Leu-Ile-Phe-Cys-His-Ser-Lys-Lys-Lys- Cys-Asp-Glu-Leu-Ala-Ala-Lys-Leu-Val-Ala-Leu-Gly-Ile-Asn-Ala-Val-Ala-Tyr-Tyr-Arg-Gly-Leu-Asp-Val-Ser-Val-Ile-Pro-Thr-Ser-Gly-Asp-Val-Val-Val-Val-Ala-Thr-Asp-Ala-Leu-Met-Thr-Gly-Tyr-Thr-Gly-Asp-Phe-Asp-Ser-Val-Ile-Asp-Cys-Asn-Thr-Cys-Val, (PepB; SEQ ID NO.:7), and Ala-Leu-Gly-His-Glu-Gly-Glu-Ile-Pro-Phe-Tyr-Gly-Lys-Ala-Ile-Pro-Leu-Ala-Phe-Ile-Lys-Gly-Gly-Arg-His-Leu-Ile-Phe-Cys-His-Ser-Lys-Lys-Lys-Cys-Asp-Glu-Leu-Ala-Ala-Ala-Leu-Arg-Gly-Met-Gly-Val-Asn-Ala-Val-Ala-Tyr-Tyr-Arg-Gly-Leu-Asp-Val-Ser-Val-Ile-Pro-Thr-Gln-Gly-Asp-Val-Val-Val-Val-Ala-Thr-Asp-Ala-Leu-Met-Thr-Gly-Tyr-Thr-Gly-Asp-Phe-Asp-Ser-Val-Ile-Asp-Cys-Asn-Val-Ala-Val, (PepC; SEQ ID NO:12), as well as analogs, segments, polymers and mixtures thereof.

The branched peptides are represented by the formula

[peptide]$_2$X

[peptide]$_4$X$_2$X

[peptide]$_8$X$_4$X$_2$X

[peptide]$_{16}$X$_8$X$_4$X$_2$X where X is an amino acid or an amino acid analog having two amino groups and one carboxyl group with each group being capable of forming a peptide bond linkage, and where the peptide moiety, i.e., [peptide], comprises at least one epitope which is specifically immunoreactive with antibodies against HCV. The peptide moiety further comprises at least one cluster of from about 3 to about 20 contiguous amino acids from the sequences:

Glu-Ile-Leu-Arg-Lys-Ser-Arg-Arg-Phe-Ala-Gln-Ala-Leu-Pro-Val-Trp-Ala-Arg-Pro-Asp-Tyr-Asn-Pro-Pro-Leu-Val-Glu-Thr-Trp-Lys-Lys-Pro-Asp-Tyr-Glu-Pro-Pro-Val-Val-His-Gly-Cys-Pro-Leu-Pro-Pro-Pro-Lys-Ser-Pro-Pro-Val-Pro-Pro-Pro-Arg-Lys-Lys-Arg-Thr, (Pep11; SEQ ID NO:20),

Glu-Ile-Pro-Phe-Tyr-Gly-Lys-Ala-Ile-Pro-Leu-Glu-Val-Ile-Lys-Gly-Gly-Arg-His-Leu-Ile-Phe-Cys-His-Ser-Lys-Lys-Lys-Cys-Asp-Glu-Leu-Ala-Ala-Lys-Leu-Val-Ala-Leu, (Pep18; SEQ ID NO:21),

Ser-Gly-Lys-Pro-Ala-Ile-Ile-Pro-Asp-Arg-Glu-Val-Leu-Tyr-Arg-Glu-Phe-Asp-Glu-Met-Glu-Glu-Cys-Ser-Gln-His-Leu-Pro-Tyr-Ile-Glu-Gln-Gly-Met-Met-Leu-Ala-Glu-Gln-Phe-Lys-Gln-Lys-Ala-Leu-Gly-Leu, (IIH; SEQ ID NO:22),

Ser-Thr-Ile-Pro-Lys-Pro-Gln-Arg-Lys-Thr-Lys-Arg-Asn-Thr-Asn-Arg-Arg-Pro-Gln-Asp-Val-Lys-Phe-Pro-Gly-Gly-Gly-Gln-Ile-Val-Gly-Gly-Val-Tyr-Leu-Leu-Pro-Arg-Arg-Gly-Pro-Arg-Leu-Gly-Val-Arg-Ala-Thr-Arg-Lys-Thr-Ser-Glu-Arg-Ser-Gln-Pro-Arg-Gly-Arg-Arg, (VIIIE; SEQ ID NO:23),

Ala-Leu-Ser-Thr-Thr-Gly-Glu-Ile-Pro-Phe-Tyr-Gly-Lys-Ala-Ile-Pro-Leu-Glu-Val-Ile-Lys-Gly-Gly-Arg-His-Leu-Ile-Phe-Cys-His-Ser-Lys-Lys-Lys-Cys-Asp-Glu-Leu-Ala-Ala-Lys-Leu-Val-Ala-Leu-Gly-Ile-Asn-Ala-Val-Ala-Tyr-Tyr-Arg-Gly-Leu-Asp-Val-Ser-Val-Ile-Pro-Thr-Ser-Gly-Asp-Val-Val-Val-Val-Ala-Thr-Asp-Ala-Leu-Met-Thr-Gly-Tyr-Thr-Gly-Asp-Phe-Asp-Ser-Val-Ile-Asp-Cys-Asn-Thr-Cys-Val, (PepB),

Ala-Leu-Gly-His-Glu-Gly-Glu-Ile-Pro-Phe-Tyr-Gly-Lys-Ala-Ile-Pro-Leu-Ala-Phe-Ile-Lys-Gly-Gly-Arg-His-Leu-Ile-Phe-Cys-His-Ser-Lys-Lys-Lys-Cys-Asp-Glu-Leu-Ala-Ala-Ala-Leu-Arg-Gly-Met-Gly-Val-Asn-Ala-Val-Ala-Tyr-Tyr-Arg-Gly-Leu-Asp-Val-Ser-Val-Ile-Pro-Thr-Gln-Gly-Asp-Val-Val-Val-Val-Ala-Thr-Asp-Ala-Leu-Met-Thr-Gly-Tyr-Thr-Gly-Asp-Phe-Asp-Ser-Val-Ile-Asp-Cys-Asn-Val-Ala-Val, (PepC), or a sequence corresponding to one of these sequences which is from a corresponding region in a strain or isolate of HCV. Moreover, when the peptide moiety comprises two or more clusters, the clusters are joined by a linking group or when the clusters each have a sequence from a different one of the above sequences, then the clusters can be joined directly or joined by a linking group.

When the peptide moiety contains sequences from different ones of the above sequences, such peptides are referred to as hybrid peptides. Hybrid peptides can but do not necessarily contain clusters. Clusters in hybrid peptides can be joined directly or by linking groups. In the hybrid peptides, the length of contiguous amino acids from each of the sequences can be up to about 60 residues.

Another aspect of the invention provides a method of detecting antibodies to HCV or diagnosis of HCV infection or NANBH by using an immunoeffective amount of the subject peptide composition in an immunoassay procedure, and particularly in an ELISA procedure, or a passive hemagglutination (PHA) assay. Immunoassays and kits for the detection and diagnosis of NANBH and HCV infection are also provided.

Yet another aspect of this invention provides vaccines using the subject branched hybrid and cluster peptides or peptide compositions as immunogens to prevent or therapeutically treat NANBH or HCV infection. A method of preventing or treating NANBH or HCV infection using these vaccine compositions is also provided.

DETAILED DESCRIPTION OF THE INVENTION

In accordance with the present invention, extensive serological analysis has led to the refinement and further definition of immunoreactive peptides that are useful in the detection and diagnosis of NANBH and HCV infection. This analysis has established that effective diagnostic peptides for NANBH or HCV infection include linear as well as branched peptides from NS3. The peptides, optionally branched, can be hybrids of peptides containing one or more HCV epitopes from different peptides, referred to herein as hybrid peptides. Further, the peptides of this invention also include those peptides having at least one epitope which is specifically immunoreactive with antibodies against HCV and having a peptide moiety which comprises one or more clusters of about 3 to about 20 contiguous amino acids from the peptides designated as Pep3, Pep8, Pep11, Pep18, Pep25, IIH, IIID, V, VIIIE, PepA, PepB, PepC or a homologous peptide from a corresponding region in another strain or isolate of HCV. The amino acid sequences of the peptides designated as Pep3, Pep8, Pep25, IIID, V, and PepA are provided in U.S. Ser. No. 946,054, filed Sep. 15, 1992, which is incorporated herein by reference. In addition, when the peptide moiety of these peptides, also referred to herein as cluster peptides, contain two or more clusters, then the clusters are joined by a linking group. The linking group consists of, but is not limited to, one or more naturally occurring amino acids, one or more unnatural amino acids, or one or more amino acid analogues which can form peptidyl bonds (or peptidyl-like bonds) and are stable to the conditions employed during peptide synthesis. In the case of hybrid peptides that contain clusters, the clusters can be joined directly or can be joined by a linking group.

In addition the linear peptides of NS3 can be modified to consist of the peptide moieties of the hybrid peptides or the cluster peptides as herein defined.

The sequences of the peptides subjected to detailed serological analysis, and from which the peptide moieties of the subject linear and branched peptides are derived, are set forth below:

| | |
|---|---|
| Glu—Ile—Leu—Arg—Lys—Ser—Arg—Arg—Phe—Ala—Gln—Ala—Leu—Pro—Val—Trp—Ala—Arg—Pro—Asp—Tyr—Asn—Pro—Pro—Leu—Val—Glu—Thr—Trp—Lys—Lys—Pro—Asp—Tyr—Glu—Pro—Pro—Val—Val—His—Gly—Cys—Pro—Leu—Pro—Pro—Pro—Lys—Ser—Pro—Pro—Val—Pro—Pro—Pro—Arg—Lys—Lys—Arg—Thr—X, | Pep11 |
| Glu—Ile—Pro—Phe—Tyr—Gly—Lys—Ala—Ile—Pro—Leu—Glu—Val—Ile—Lys—Gly—Gly—Arg—His—Leu—Ile—Phe—Cys—His—Ser—Lys—Lys—Lys—Cys—Asp—Glu—Leu—Ala—Ala—Lys—Leu—Val—Ala—Leu—X, | Pep18 |

-continued

Ser—Gly—Lys—Pro—Ala—Ile—Ile—Pro—Asp—Arg—Glu—Val—Leu—Tyr—Arg—     IIIH
Glu—Phe—Asp—Glu—Met—Glu—Glu—Cys—Ser—Gln—His—Leu—Pro—Tyr—Ile—
Glu—Gln—Gly—Met—Met—Leu—Ala—Glu—Gln—Phe—Lys—Gln—Lys—Ala—Leu—
Gly—Leu—X,

Ser—Thr—Ile—Pro—Lys—Pro—Gln—Arg—Lys—Thr—Lys—Arg—Asn—Thr—Asn—     VIIIE
Arg—Arg—Pro—Gln—Asp—Val—Lys—Phe—Pro—Gly—Gly—Gly—Gln—Ile—Val—
Gly—Gly—Val—Tyr—Leu—Leu—Pro—Arg—Arg—Gly—Pro—Arg—Leu—Gly—Val—
Arg—Ala—Thr—Arg—Lys—Thr—Ser—Glu—Arg—Ser—Gln—Pro—Arg—Gly—Arg—
Arg—X,

Ala—Leu—Ser—Thr—Thr—Gly—Glu—Ile—Pro—Phe—Tyr—Gly—Lys—Ala—Ile—     PepB
Pro—Leu—Glu—Val—Ile—Lys—Gly—Gly—Arg—His—Leu—Ile—Phe—Cys—His—
Ser—Lys—Lys—Cys—Asp—Glu—Leu—Ala—Ala—Lys—Leu—Val—Ala—Leu—
Gly—Ile—Asn—Ala—Val—Ala—Tyr—Tyr—Arg—Gly—Leu—Asp—Val—Ser—Val—
Ile—Pro—Thr—Ser—Gly—Asp—Val—Val—Val—Val—Ala—Thr—Asp—Ala—Leu—
Met—Thr—Gly—Tyr—Thr—Gly—Asp—Phe—Asp—Ser—Val—Ile—Asp—Cys—Asn—
Thr—Cys—Val—X,

Ala—Leu—Gly—His—Glu—Gly—Glu—Ile—Pro—Phe—Tyr—Gly—Lys—Ala—Ile—     PepC
Pro—Leu—Ala—Phe—Ile—Lys—Gly—Gly—Arg—His—Leu—Ile—Phe—Cys—His—
Ser—Lys—Lys—Cys—Asp—Glu—Leu—Ala—Ala—Ala—Leu—Arg—Gly—Met—
Gly—Val—Asn—Ala—Val—Ala—Tyr—Tyr—Arg—Gly—Leu—Asp—Val—Ser—Val—
Ile—Pro—Thr—Gln—Gly—Asp—Val—Val—Val—Val—Ala—Thr—Asp—Ala—Leu—
Met—Thr—Gly—Tyr—Thr—Gly—Asp—Phe—Asp—Ser—Val—Ile—Asp—Cys—Asn—
Val—Ala—Val, or a homologous peptide from the corresponding region in another strain or isolate of HCV, wherein X is —OH or —NH$_2$, and analogues and segments of these peptides.

As used herein a linear peptide has about 50 to about 100 amino acids, preferably about 60 to about 90 amino acids, and more preferably about 75 to about 90 amino acids. The linear peptides can contain clusters of HCV sequences as defined herein provided such peptides retain specific immunoreactivity with HCV antibodies.

As used herein a "cluster" is a sequence from 3 to about 20 contiguous amino acids from one of the peptide sequences described herein or an analog or segment thereof. In a preferred embodiment, a cluster has a sequence of 3 to 9 contiguous amino acids.

The linear, the branched hybrid and the cluster peptides of the present invention including their analogues and segments are useful for the detection of antibodies to HCV in body fluids, the diagnosis of NANBH, and for the vaccination of healthy mammals, particularly humans, to stimulate the production of antibodies to HCV, including neutralizing or protective antibodies.

The subject linear and branched peptides can comprise combinations or segments, i.e., longer or shorter peptide chains by having more amino acids, including unnatural amino acids, added to the terminal amino acids, or by having amino acids removed from either terminal end. For example, the sequence KKK (Lys-Lys-Lys) can be added to the amino terminus of any of these peptides. For branched peptides, an M (methionine) residue can be placed at the carboxy terminus of the peptide moiety, i.e. between the peptide moiety and the branch structure.

As used herein "segments" means a shorter region of a parent peptide which retains an epitope effective in detecting NANBH-associated antibodies. For example, L1A is a segment of PepB, its parent peptide. A segment can be derived from either end of its parent peptide or from an internal sequence of its parent peptide.

The subject branched peptides can also comprise analogues to accommodate strain-to-strain variation among different isolates of HCV or other substitutions in the prescribed sequences which do not affect immunogenicity of the epitope. HCV is indicated to have frequent mutations. Several variant strains/isolates are known to exist, such as PT, J, J1 and J4 [Houghton, 1989; Okamoto, 1990; Houghton, 1990; and Karo, 1990] and it is expected that other variant strains also exist. Adjustments for conservative substitutions and selection among the alternatives where non-conservative substitutions are involved, can be made in the prescribed sequences. The analogues of the linear and branched synthetic peptides, especially the hybrid peptides, can therefore comprise substitutions, insertions and/or deletions of the recited amino acids of the above sequence to accommodate the various strains, as long as the immunoreactivity recognizable by the antibodies to HCV is preserved. In addition, the substitutions, insertions, and deletions in analogues need not be encoded by other HCV strains provided that such changes produce peptides which preserve immunoreactivity with HCV. The substitutions and insertions can be accomplished with naturally-occurring amino acids, unnatural amino acids or amino acid analogues capable of forming peptidyl bonds or peptide-like bonds (e.g., peptide thiol analogues). Analog peptides in accordance with this invention are synthesized and tested against an HCV serum panel to determine the immunoreactivity of the peptide as described hereinbelow.

Further, with appropriate amino acid modification or substitutions, it is expected that various peptide analogues based on the prescribed amino acid sequences can be synthesized with properties giving rise to lower background readings or better binding capacity to solid phases useful for HCV antibody screening assays. In particular, peptides containing unnatural amino acids can significantly reduce background readings.

The subject linear or branched peptides can also be used to form conjugates, i.e., the peptides can be coupled directly or indirectly, by methods known in the art, to carrier proteins such as bovine serum albumin (BSA), human serum albumin (HSA), or to red blood cells or latex particles.

As used herein, natural amino acids are the 20 amino acids commonly found in proteins (i.e. alanine, aspartic acid, asparagine, arginine, cysteine, glycine, glutamine, glutamic acid, histidine, isoleucine, leucine, lysine, methionine, phenylalanine, proline, serine, threonine, tyrosine, tryptophan and valine). As used herein the natural amino acids also include the D- and L- forms of such amino acids.

As used herein "unnatural amino acids" include both D- and L- forms of any other amino acids whether found in a protein, whether found in nature or whether synthetically produced. Unnatural amino acids can include, but are not limited to, β-alanine, ornithine, norleucine, norvaline, hydroxyproline, thyroxine, gamma-amino butyric acid, homoserine, citrulline and the like.

The linear peptides of this invention are represented by the formula

[peptide]'Y wherein Y is —OH or —NH$_2$, and include analogues, segments, mixtures, conjugates and polymers of these linear peptides. The peptides comprise at least one epitope which is specifically immunoreactive with antibodies against HCV. Furthermore, the peptide moiety of the linear peptides can be defined as set forth below for the peptide moiety of the branched peptides, i.e. the linear peptides can contain clusters or hybrids of HCV epitopes.

The branched peptides of the present invention are represented by one of the formulae:

[peptide]$_2$X

[peptide]$_4$X$_2$X

[peptide]$_8$X$_4$X$_2$X

[peptide]$_{16}$X$_8$X$_4$X$_2$X wherein X is an amino acid or an amino acid analog having two amino groups and one carboxyl group, each group capable of forming a peptide bond linkage. Preferably X is lysine or a lysine analog such as ornithine. The amino acid analog can be an α-amino acid, a β-amino acid, or any other either natural or non-natural amino acid with two amino groups and one carboxyl group available for forming peptide bonds. Preferred branched peptides of the invention are dimers, tetramers and octamers, especially those having a branching core structure composed of lysine, i.e. where X is lysine. Branched dimers are especially preferred.

The peptide moiety of the branched peptides can vary in length from about 10 to about 100 amino acids residues. Preferably the peptide moieties contain about 17 to about 60 amino acid residues. Moreover, the hybrid and cluster peptide moieties can be optimized to the minimal overall length necessary to contain an epitope effective in detecting NANBH-associated antibodies yet still retain the superior sensitivity and selectivity of the present invention.

The preferred peptides of the present invention are provided in Table 1. The source of each peptide is provided in Table 2.

TABLE 1

PEPTIDES[a,b,c]

HYBRID PEPTIDES WITH OR WITHOUT CLUSTERS

3KH8  KKKSGKPTIIPDRELYREFDMEDCSQHLPYzDQGMMLAENFKQKAVGLVKFPGGGNI—DIM

CLUSTER PEPTIDES (LINEAR OR BRANCHED)

C6C  PLvETWKKPEYEPPVVH—DIM
3KC10C  KKKSGKPTIIPDRELYREFDMEDCSQHLPYzDQGMMLAENFKQKAVGLVKFPGGGNI—DIM (PLvETWKKPEYEPPVVH—DIM)
C11  KKKIPKPNoKTKRNTQRRPNDvKFPGGGNtvGGVYLVPRRGPRzGLRATRKTTERSQpRGRR—DIM
C12  PLvETWKKPEYEPPVvHGCPLPPpKSPPVPPpRKKRT—DIM
C13  KAvPLEvVKGGRHLIFCHSKKKCDELAAKLVALGINAVAYYRGLDVSVIPTSGDVVVVATDALMTGYTGDFDSVIDCNTCV—NH
C14A  GRHLIvCHTKKKCDELAAKLVALGINAVAYYRGLDVSVIPTSGDVVVVATDALMTGYTGDFDSVIDCNTCV—NH
3KC14B  KAvPLEvVKGGRHLIvCHTKKKCDEzAAKLvALGINAvAYYRGLDvSVIPTSGEVvvVATDAzMTGYTGEFDSvIDCNTCV—NH
  KKKKAvPLEvVKGGRHLIvCHTKKKCDEzAAKLvALGINAvAYYRGLDvSVIPTSGEvVvVATDAzMTGYTGEFDSvIDCNTCV—DIM

LINEAR PEPTIDES

L1A  KKKCDELAAKLVALGINAVAYYRGLDVSVIPTSGDVVVVATDALMTGYTGDFDSVIDCNTCV—NH
L1B  GRHLIFCHSKKKCDELAAKLVALGINAVAYYRGLDVSVIPTSGDVVVVATDALMTGYTGDFDSVIDCNTCV—NH
L1C  KAIPLEVIKGGRHLIFCHSKKKCDELAAKLVALGINAVAYYRGLDVSVIPTSGDVVVVATDALMTGYTGDFDSVIDCNTCV—NH
L1D  ALSTTGEIPFYGKAIPLEVIKGGRHLIFCHSKKKCDELAAKLVALGINAVAYYRGLDVSVIPTSGDVVVVATDALMTGYTGDFDSVIDCNTCV—NH
3KL1C  KKKKAIPLEVIKGGRHLIFCHSKKKCDELAAKLVALGINAVAYYRGLDVSVIPTSGDVVVVATDALMTGYTGDFDSVIDCNTCV—NH
L2A  KKKCDELAAALRGMGVNAVAYYRGLDVSVIPTGDVVVVATDALMTGYTGDFDSVIDCNVAV—NH
L2B  GRHLIFCHSKKKCDELAAALRGMGVNAVAYYRGLDVSVIPTQGDVVVVATDALMTGYTGDFDSVIDCNVAV—NH
L2C  KAIPLAFIKGGRHLIFCHSKKKCDELAAALRGMGVNAVAYYRGLDVSVIPTQGDVVVVATDALMTGYTGDFDSVIDCNVAV—NH
L2D  ALGHEGEIPFYGKAIPLAFIKGGRHLIFCHSKKKCDELAAALRGMGVNAVAYYRGLDVSVIPTQGDVVVVATDALMTGYTGDFDSVIDCNVAV—NH
L3A  KKKCDELAAALRGMGVNAVAYYRGLDVSVIPTQGDVVVVATDALMTGYTGDFDSVIDCNVCV—NH
L3B  GRHLIFCHSKKKCDELAAALRGMGVNAVAYYRGLDVSVIPTQGDVVVVATDALMTGYTGDFDSVIDCNVCV—NH
L3C  KAIPLAFIKGGRHLIFCHSKKKCDELAAALRGMGVNAVAYYRGLDVSVIPTQGDVVVVATDALMTGYTGDFDSVIDCNVCV—NH
L4A  KKKCDELAAKLVALGINAVAYYKGLDVSVIPTSGDTDALMTGYTGDFDSVIDC—NH
L4B  GKHLIFCSKKKCDELAAKLVALGINAVAYYKGLDVSVIPTSGDTDALMTGYTGDFDSVDC—NH
L4C  KAIPLEVIKGGKHLIFCHSKKKCDELAAKLVALGINAVAYYKGLDVSVIPTSGDTDALMTGYTGDFDSVDC—NH
3KL4C  KKKKAIPLEVIKGGKLIFCHKKKCDELAAKLVALGINAVAYYKGLDVSVIPTSGDTDALMTGYTGDFDSVIDC—NH

[a]Abbreviations: The amino acid sequences are provided in one letter code except that unnatural amino acids are indicated by: v, norvaline; z, norleucine; p, hydroxyproline; o, ornithine. Other abbreviations are DIM, lysine dimer; OCT, lysine octamer.
[b]For branched peptides, the branched core is composed of lysines residues, e.g., 1 Lysine for dimer peptides (DIM) and 7 Lysines for octamer peptides (OCT).
[c]The sequences Lsiting for these peptides are set forth: C12, SEQ ID NO:1; C13, SEQ ID NO:2; C14A, SEQ ID NO 3; L1A, SEQ ID NO 4; L1B, SEQ ID NO 5; L1C, SEQ ID NO 6; L1D, SEQ ID NO 7; 3KL1C, SEQ ID NO 8; L2A, SEQ ID NO 9; L2B, SEQ ID NO 10; L2C, SEQ ID NO 11; L2D, SEQ ID NO 12; L3A, SEQ ID NO 13; L38, SEQ ID NO 14; L3C, SEQ ID NO 15; L4A, SEQ ID NO 16; L4B, SEQ ID NO 17; L4C, SEQ ID NO 18; and 3KL4C, SEQ ID NO 19.

TABLE 2

SOURCE OF HYBRID AND CLUSTER BRANCHED PEPTIDES

| Source Peptide | Peptides from Table 1 |
|---|---|
| Pep11 | C6C, C11 |
| VIIIE | 3KC10C |
| IIH + VIIIE | 3KH8 |
| PepB | L1A, L1B, L1C, L1D, 3KL1C, L4A, L4B, L4C, 3KL4C, C12, C13, C14A, 3KC14B |
| PepC | L2A, L2B, L2C, L2D, L3A, L3B, L3C |

The peptide compositions of the present invention can be composed of one or more of the linear peptides (with or without hybrids or clusters), the branched hybrid peptides, the branched cluster peptides or any combination of such peptides. Preferably such compositions contain from one to 10 peptides, and even more preferably from one to four peptides.

In a preferred embodiment, the peptide compositions of the present invention include peptides L1C, 3KL1C, L2C, L3A, 3KL4C and C12, from PepB and PepC, and more preferably peptides L1C, 3KL1C and C12. Peptide 3KL1C is particularly useful in PHA immunoassays for detection of HCV antibodies. Other preferred peptides of the invention include peptides C6C, 3KC10C, C11 and 3KH8.

Moreover, the peptide compositions of the present invention include mixtures of peptides. The effective ratio of peptides for diagnosing or detecting NANBH or HCV present in peptide compositions containing mixtures of the subject peptides can be readily determined by one of ordinary skill in the art. Typically, these ratios range from about 1 to about 50 on a per weight basis of peptide.

A preferred peptide composition for diagnosis and detection of NANBH or HCV infection is a mixture of peptides 3KC10C dimer, C11 dimer, C12 linear and 3KH8 dimer in a weight ratio of 1:1:3:2.

To determine the efficacy of the subject peptides in detecting and diagnosing NANBH and HCV infection, the peptides are tested for their immunoreactivity with specimens previously selected through the screening of thousands of patient and normal sera for immunoreactivity with HCV. Such serum panels are commercially available and examples thereof are provided in the Examples.

The strategy for serological validation depends on the expected characteristics of the target epitopes. For example, universal immunodominant epitopes, such as the gp41 transmembrane peptide of HIV-1, can be screened by a single representative serum sample from a patient known to be infected with the virus. Epitopes that are not recognized by all infected individuals, or those for which antibody is produced late or only transiently, and especially epitopes which give rise to neutralizing antibodies, must be screened by large panels of sera. While both methods of screening can be employed in the present invention to refine the epitope analysis of HCV using the subject peptides, the latter method is particularly useful in assessing the subject peptides for superior selectivity and sensitivity.

The identification of the immunoreactive epitopes is also dependent on the panel of sera used. The more closely the panel represents the population most likely to be seropositive for an epitope, the greater the chance that the epitope will be identified and thoroughly mapped. Hence, to extend the range of reactivity of an assay comprised of previously identified epitopes, a large number of samples from individuals at risk of infection but seronegative against known epitopes should be employed for screening.

The process of "serological validation" is particularly difficult when the epitopes to be identified elicit antibodies only in a subpopulation of an infected patient group. When such epitopes become targets for identification, special attention must be paid to synthetic peptides which show very weak reactivity when tested by an enzyme immunoassay or any other immunological testing method.

In this regard, the low background absorbance of synthetic peptides, especially peptides with unnatural amino acids, allows for the precise detection of weak reactivities. In some cases, absorbances of 50 mA versus background reading are of sufficient significance and can lead to the identification of important epitopes through successive refinement of the amino acid sequence of a peptide. With good laboratory practices, consistent and reliable results can be obtained when working in the range of absorbances below 200–300 mA.

To identify highly immunoreactive HCV NS-3 peptides, more than 135 overlapping peptides with lengths from 12 to over 100 residues have been designed, synthesized and tested with a special panel of sera from patients with PT-NANBH (post-transfusion NANBH), including sera from early stages of HCV infection. Among the NS-3 peptides tested, only three long peptides, L1D, L2D and substitution analogue C12, and their related shorter segments, particularly those corresponding to L1B and L1C, were found to possess significant HCV immunoreactivity.

Through extensive serological analysis, using L1D as an example, a stretch of 15 amino acids with a sequence of YTGDFDSVIDCNTCV (amino acids 79 to 93 of SEQ ID NO:7) located at the C-terminus of L1D contains sequences that are important to the formation of a conformational epitope along with the rest of the peptide structure. At the N-terminus, a stretch of at least 10 amino acids with a sequence of KAIPLEVIKG (amino acids 13 to 22 of SEQ ID NO:7) enhances the immunoreactivity of the peptides, whereas the next 9 amino acids (GRHLIFCHS; amino acids 23 to 31 of SEQ ID NO:7) greatly enhances such immunoreactivity. Additional amino acids at the N-terminus such as ALSTTGEIPFYG (amino acids 1 to 12 of SEQ ID NO:7), though contributing to the stabilization of the conformational epitope, are optional. Moreover, certain amino acid substitutions made in this region as shown in peptide C12 do not necessarily diminish immunoreactivity. The NS-3 peptides of the present invention represent a protein structural framework which maintains the conformation of the much larger NS-3 protein and therefore forms a functional domain of NS-3. For example, cleavage at the mid-point of this domain destroys the structure and results in the loss of HCV immunoreactivity as shown in Example 2. However, when the structure of the functional domain is preserved, addition of amino acid residues at either the N- or C-terminus does not interfere with inherent immunoreactivity of the NS-3 derived peptides of this invention.

Based on the immunoreactivities of the peptides of the present invention, the subject peptides are also useful in a vaccine composition to treat or prevent NANBH or HCV infection. The peptides, alone or when coupled to a carrier or polymerized to homo or hetero dimers or higher oligomers by cysteine oxidation, by induced disulfide cross-linking, or by use of homo or hetero functional multivalent cross-linking reagents, can be introduced into normal subjects to stimulate production of antibodies to HCV in healthy mammals. Similarly the subject peptides can be formulated in a vaccine composition using adjuvants, pharmaceutically-acceptable carriers or other ingredients routinely provided in vaccine compositions. Such formulations are readily determined by one of ordinary skill in the art and include formulations for immediate release and for sustained release, e.g., microencapsulation. The present vaccines can be administered by any convenient route including subcutaneous, oral, intramuscular, intravenous, or other parenteral or enteral route. Similarly the vaccines can be administered as a single dose or divided into multiple doses for administration.

The vaccine compositions of the instant invention contain an immunoeffective amount of the subject peptides to treat or prevent NANBH or HCV infection. Such compositions in dosage unit form can contain about 0.1 µg to about 1 mg of the peptide (or mixture of peptides) per kg body weight. When delivered in multiple doses, the dosage unit form is conveniently divided into the appropriate amounts per dosage.

The advantages of using synthetic peptides are known. Since the peptides are not derived biologically from the virus, there is no danger of exposing the normal subjects who are to be vaccinated to the disease causing pathogen. The peptides can be readily synthesized using standard techniques, such as the Merrifield method of synthesis [Merrifield (1963) *J. Am. Chem. Soc.* 85:2149–2154]. Hence, there is no involvement with HCV at any time during the process of making the test reagent or the vaccine. Another problem which can be minimized by using peptides rather than recombinantly expressed proteins (or peptides) is the rate of false positive results caused by the presence of antigenic material co-purified with the HCV fusion protein. For example, certain normal individuals have antibodies to *Escherichia coli* or yeast proteins which are cross reactive with the antigenic materials from the expression system used in recombinant-based diagnostic tests. Sera from such normal individuals show a false positive reaction in such immunoassays which is eliminated in immunoassays of the present invention.

Moreover, because the peptide compositions of the present invention are synthetically prepared, the quality can be controlled and as a result, reproducibility of the test results can be assured. Also, since very small amounts of a peptide are required for each test procedure, and because the expense of preparing a peptide is relatively low, the cost of screening body fluids for antibodies to HCV, diagnosis of NANBH infection, and the preparation of a vaccine is relatively low.

The peptides and peptide compositions prepared in accordance with the present invention can be used to detect HCV infection and diagnose NANBH by using them as the test reagent in an enzyme-linked immunoadsorbent assay (ELISA), an enzyme immunodot assay, a passive hemagglutination assay (e.g., PHA test) or other well-known immunoassays. In accordance with the present invention, any suitable immunoassay can be used with the subject peptides. Such techniques are well known to the ordinarily skilled artisan and have been described in many standard immunology manuals and texts, see for example, by Harlow et al. (1988) *Antibodies: A Laboratory Manual,* Cold Spring Harbor Laboratory Press, Cold Spring Harbor, N.Y., 726 pp. In a preferred embodiment, the immunoassay is an ELISA using a solid phase coated with the peptide compositions of the present invention. ELISA techniques are well known in the art. In another preferred embodiment the immunoassay is a PHA assay.

The immunoassays of the present invention are used to screen body fluids and tissues for the presence of NANBH or HCV and thereby to detect such agents and aid the practitioner in diagnosis of NANBH or HCV infection. The body fluids which can be subjected to such screening include blood and blood fractions (e.g. serum), saliva, or any other fluid which contains antibodies against HCV.

Another aspect of the present invention is directed to a kit for the detection and diagnosis of NANBH or HCV infection in mammalian body fluids (e.g. serum, tissue extracts, tissue fluids), in vitro cell culture supernatants, and cell lysates. The kit can be compartmentalized to receive a first container adapted to contain one or more of the peptides (i.e. a peptide composition) of this invention.

Preferably the kit of this invention is an ELISA or a PHA test kit for detection or diagnosis of NANBH or HCV infection. For an ELISA test kit, the kit contains (a) a container (e.g., a 96-well plate) having a solid phase coated with one of the subject peptide compositions; (b) a negative control sample; (c) a positive control sample; (d) specimen diluent and (e) antibodies to human IgG, which antibodies are labelled with a reporter molecule. If the reporter molecule is an enzyme, then the kit also contains a substrate for said enzyme.

In an exemplified use of the subject kit, a sample to be tested is contacted with a mammalian body fluid, diluted in sample diluent if necessary, for a time and under conditions for any antibodies, if present, to bind to the peptide contained in the container. After removal of unbound material (e.g. by washing with sterile phosphate buffered saline), the secondary complex is contacted with labelled antibodies to human IgG. These antibodies bind to the secondary complex to form a tertiary complex and, since the second antibodies are labeled with a reporter molecule, when subjected to a detecting means, the tertiary complex is detected. The reporter molecule can be an enzyme, radioisotope, fluorophore, bioluminescent molecule, chemiluminescent molecule, biotin, avidin, streptavidin or the like. For ELISA the reporter is preferably an enzyme.

The examples serve to illustrate the present invention and are not to be used to limit the scope of the invention.

EXAMPLE 1

ELISA Assay Method

The wells of 96-well plates were coated separately for 1 hour at 37° with 5 µg/ml of peptide using 100 µL per well in 10 mM $NaHCO_3$ buffer, pH 9.5 unless noted otherwise.

The peptide-coated wells were incubated with 250 µL of 3% by weight of gelatin in PBS in 37° C. for 1 hour to block non-specific protein binding sites, followed by three washes with PBS containing 0.05% by volume of TWEEN 20 and dried. The test specimens containing HCV antibody positive patient sera were diluted 1:20 volume to volume with PBS containing 20% by volume normal goat serum, 1% by weight gelatin and 0.05% by volume TWEEN 20. 200 μL of the diluted specimens were added to each of the wells and allowed to react for 15 minutes at 37° C.

The wells were then washed six times with 0.05% by volume TWEEN 20 in PBS in order to remove unbound antibodies. Horseradish peroxidase conjugated goat anti-human IgG was used as a second antibody tracer to bind with the HCV antibody-peptide antigen complex formed in positive wells. 100 μL of peroxidase labeled goat anti-human IgG at a dilution of 1:1800 in 1% by volume normal goat serum, 0.05% by volume TWEEN 20 in PBS was added to each well and incubated at 37° C. for another 15 minutes.

The wells were washed six times with 0.05% by volume TWEEN 20 PBS to remove unbound antibody and reacted with 100 μL of the substrate mixture containing 0.04% by weight orthophenylenediamine (OPD) and 0.12% by volume hydrogen peroxide in sodium citrate buffer, pH 5.0. This substrate mixture was used to detect the peroxidase label by forming a colored product. Reactions were stopped by the addition of 100 μL of 1.0M $H_2SO_4$ and the $A_{492}$nm measured.

EXAMPLE 2
NS-3 Epitope Mapping

Extensive serological analysis was used to locate useful epitopes in NS-3. One example establishing the importance of length in an NS-3 epitope is illustrated with peptides L1C, T5 series, T6 series, T7 and T8. L1C is an 81-mer containing the reactive epitope. The T5 and T6 series peptides which are non-reactive with HCV sera consist of a maximum of 39 amino and 45 carboxy terminal residues of L1C, respectively. Peptides T7 and T8 which are also non-reactive span the central 47 and 25 amino acids of L1C, respectively. The sequence of L1C is provided in Table 1. The remaining sequences are:

| | |
|---|---|
| T5A, | LIFCHSKKKCDELAAKLVAL—NH |
| T5B, | KGGRHLIFCHSKKKCDELAAKLVAL—NH |
| T5C, | AIPLEVIKGGRHLIFCHSKKKCDELAAKLVAL—NH |
| T5D, | EIPFYGKAIPLEVIKGGRHLIFCHSKKKCDELAAKLVAL—NH |
| T6A, | DVVVVATDALMTGYTGDFDSVIDCNTC—NH |
| T6B, | DVSVIPTSGDVVVVATDALMTGYTGDFDSVIDCNTC—NH |
| T6C, | NAVAYYRGLDVSVIPTSGDVVVVATDALMTGYTGDFDSVIDCNTC—NH |
| T7, | KKKCDELAAKLVALGINAVAYYRGLDVSVIPTSGDVVVVATDALMTG—NH |
| T8, | KLVALGINAVAYYRGLDVSVIPTSG—NH |

The immunoreactivity of these peptides was tested as described in Example 1 against a panel of commercially available sera from HCV patients known to have reactivity against the NS-3 protein as determined primarily by recombinant immunoblotting analysis (RIBA, trademark). The results shown in Table 3 indicate that none of the T5, T6, T7 or T8 peptides are reactive with such sera, whereas L1C, spanning that region is strongly reactive. Similar results have been obtained with a large number of sera from HCV patients.

TABLE 3

| | Absorbence at 492 nm[a] | | | | | | | | | |
|---|---|---|---|---|---|---|---|---|---|---|
| Sample | T5A | T5B | T5C | T5D | T6A | T6B | T6D | T7 | T8 | L1C |
| 1 | 0.017 | 0.041 | 0.025 | 0.166 | 0.013 | 0.019 | 0.018 | — | — | 0.740 |
| 4 | 0.006 | 0.008 | 0.008 | 0.040 | 0.005 | 0.006 | 0.012 | — | — | 0.230 |
| 6 | 0.007 | 0.008 | 0.008 | 0.024 | 0.013 | 0.064 | 0.086 | — | — | 2.104 |
| 7 | 0.062 | 0.069 | 0.031 | 0.015 | 0.093 | 0.025 | 0.017 | — | — | 1.973 |
| 8 | 0.033 | 0.019 | 0.046 | 0.250 | 0.055 | 0.026 | 0.026 | 0.287 | — | 2.599 |
| A | — | — | — | 0.029 | — | — | 0.016 | 0.017 | 0.200 | 2.288 |
| B | — | — | — | 0.299 | — | — | 0.080 | — | 0.031 | 1.809 |

[a]"—" indicates the sample was not tested.

EXAMPLE 3
NS-3 epitopes Detected by L1C on Seroconversion Panels

The peptide L1C was used to evaluate its ability to detect HCV antibodies on two seronconversion panels known for immunoreactivity with NS-3 and derived from blood trasnfusion recipients who subsequently contracted NANBH from an HCV-positive donor. The RIBA HCV test system, 2nd generation (Chiron Corporation) assays were conducted according to manufacturer's instructions and L1C peptide assays were conducted as described in Example 1.

Both seroconversion panels contain samples that were found to have specific antibodies to HCV NS-3 protein as determine by RIBA and shown in Table 4. The L1C peptide specifically detected NS-3 antibodies at 105 and 181 days post transfusion (Table 4). These results are independent of whether the recipient had acute or chronic NANBH. Accordingly, L1C provides a sensitive probe for detection of NS-3 antibodies in PT-NANBH patients.

TABLE 4

| | Elapsed | RIBAII[a] | | | | L1C |
|---|---|---|---|---|---|---|
| Sample | Days | 5-1-1 | C100-3 | c33c | c22-3 | Abs[b] |
| HCV Pos. | Donor | — | +2 | +3 | +4 | ND |
| Patient 1 | −3 | | | | | ND |

TABLE 4-continued

| Sample | Elapsed Days | RIBAII[a] 5-1-1 | C100-3 | c33c | c22-3 | L1C Abs[b] |
|---|---|---|---|---|---|---|
| (Acute) | 105 | − | − | +3 | − | 1.231 |
|  | 165 | +1 | +3 | +4 | − | 2.195 |
|  | 546 | +/− | +/− | +3 | − | 0.613 |
| Patient 2 | 0 |  |  |  |  | ND |
| (Chronic) | 103 |  |  |  |  | 0.086 |
|  | 181 |  |  |  |  | 1.013 |
|  | 307 | − | − | +3 | − | 1.591 |

[a]"−" negative; "+", positive; "±", indeterminate. Samples which were not tested are left blank.
[b]Absorbance at 492 nm. ND, not determined.

EXAMPLE 4

Serological Analysis of PepB- and PepC-Derived Peptides

To assess relative immunoreactivity with a panel of known NS-3-reactive patient sera, ELISA assays were conducted as described in Example 1 for the NS-3 peptides listed in Table 1 (i.e., excluding peptides C6C, 3KC10C, C11 and 3KH8). The results shown in Table 5 indicate that all the tested peptides exhibited substantial immunoreactivity.

TABLE 5

| Sample | L1A* | L1B | L1C | 3KL1C | L1D | L2A | L2B |
|---|---|---|---|---|---|---|---|
| Blank | 0.048 | 0.056 | 0.048 | 0.051 | 0.047 | 0.048 | 0.048 |
| NRC | 0.030 | 0.035 | 0.030 | 0.039 | 0.024 | 0.108 | 0.156 |
| HCV 3-1 | 2.264 | 2.392 | 2.649 | 2.626 | 1.531 | 0.058 | 0.559 |
| HCV 3-5 | 0.146 | 0.419 | 1.457 | 2.424 | 0.271 | 0.084 | 0.925 |
| HCV 3-13 | 0.904 | 2.200 | 2.270 | 2.504 | 1.137 | 0.218 | 0.858 |
| HCV 3-14 | 0.303 | 0.261 | 1.542 | 2.347 | 0.275 | 0.309 | 0.862 |
| HCV 3-16 | 0.227 | 0.230 | 1.498 | 2.402 | 0.179 | 0.124 | 1.615 |
| HCV 3-17 | 0.677 | 0.842 | 1.754 | 2.559 | 0.427 | 0.333 | 2.089 |
| HCV 3-19 | 0.325 | 0.293 | 1.725 | 2.514 | 0.279 | 0.097 | 1.279 |
| HCV 3-20 | 1.618 | 2.428 | 2.394 | 2.724 | 1.862 | 0.125 | 2.205 |
| HCV 3-21 | 1.933 | 2.480 | 2.675 | 2.357 | 2.036 | 0.430 | 2.503 |
| HCV 3-24 | 1.807 | 2.554 | 2.513 | 2.812 | 1.100 | 0.856 | 0.799 |
| HCV 3-25 | 0.673 | 1.534 | 1.640 | 2.325 | 0.398 | 0.049 | 0.434 |
| HCV 3-28 | 1.850 | 2.400 | 2.870 | 2.927 | 1.481 | 0.079 | 1.187 |
| HCV 3-29 | 1.129 | 1.856 | 2.354 | 2.549 | 1.413 | 0.064 | 0.911 |
| HCV 3-30 | 1.279 | 2.288 | 2.833 | 2.461 | 1.801 | 0.750 | 1.969 |
| HCV 3-34 | — | 0.335 | 0.988 | 1.505 | — | — | — |
| HCV 3-38 | 1.722 | 2.091 | 2.448 | 2.382 | 1.390 | 0.092 | 1.507 |
| HCV 3-39 | 1.098 | 1.900 | 2.245 | 2.384 | 0.564 | 0.055 | 0.641 |
| HCV 3-40 | 1.695 | 2.401 | 2.476 | 2.703 | 1.495 | 0.115 | 1.611 |
| HCV 3-41 | 1.439 | 2.350 | 2.426 | 2.405 | 1.215 | 0.170 | 1.484 |

| Sample | L2C | L2D | L3A | L3B | L3C | L4A | L4B |
|---|---|---|---|---|---|---|---|
| Blank | 0.048 | 0.048 | 0.056 | 0.06 | 0.05 | 0.053 | 0.061 |
| NRC | 0.149 | 0.174 | 0.090 | 0.03 | 0.037 | 0.026 | 0.017 |
| HCV 3-1 | 1.441 | 1.689 | 0.187 | 0.194 | 0.887 | 0.690 | 2.214 |
| HCV 3-5 | 0.441 | 0.549 | 1.008 | 0.139 | 0.077 | 0.086 | 0.049 |
| HCV 3-13 | 1.089 | 1.375 | 2.099 | 0.232 | 0.399 | 0.195 | 0.065 |
| HCV 3-14 | 0.504 | 0.599 | 1.831 | 0.356 | 0.186 | 0.174 | 0.098 |
| HCV 3-16 | 0.416 | 0.745 | 2.200 | 0.338 | 0.201 | 0.143 | 0.035 |
| HCV 3-17 | 1.007 | 1.143 | 2.520 | 1.272 | 0.535 | 0.275 | 0.150 |
| HCV 3-19 | 1.364 | 1.430 | 1.961 | 0.238 | 0.747 | 0.104 | 0.048 |
| HCV 3-20 | 2.364 | 2.258 | 2.333 | 1.544 | 1.653 | 0.347 | 0.150 |
| HCV 3-21 | 2.499 | 2.585 | 2.029 | 2.177 | 2.157 | 0.224 | 0.077 |
| HCV 3-24 | 1.525 | 1.872 | 2.639 | 1.396 | 0.718 | 2.220 | 2.316 |
| HCV 3-25 | 0.068 | 0.163 | 1.712 | 0.216 | 0.041 | 0.121 | 0.255 |
| HCV 3-28 | 2.286 | 2.160 | 2.177 | 0.486 | 1.592 | 0.879 | 1.790 |
| HCV 3-29 | 0.173 | 0.409 | 1.997 | 0.517 | 0.060 | 0.218 | 0.270 |
| HCV 3-30 | 1.980 | 2.183 | 2.484 | 0.532 | 1.133 | 0.207 | 0.419 |
| HCV 3-34 | — | — | — | 0.243 | 0.117 | 0.056 | 0.013 |
| HCV 3-38 | 1.829 | 2.024 | 1.403 | 0.875 | 1.189 | 1.278 | 1.432 |
| HCV 3-39 | 0.157 | 0.296 | 1.575 | 0.436 | 0.097 | 0.365 | 0.790 |
| HCV 3-40 | 1.093 | 1.147 | 2.374 | 0.963 | 0.719 | 0.414 | 1.373 |
| HCV 3-41 | 0.465 | 0.983 | 2.882 | 0.788 | 0.507 | 0.648 | 1.536 |

TABLE 5-continued

| Sample | L4C | 3KL4C | C12 | C13 | C14A | 3KC14B |
|---|---|---|---|---|---|---|
| Blank | 0.056 | 0.063 | 0.055 | 0.055 | 0.054 | 0.05 |
| NRC | 0.026 | 0.016 | 0.046 | 0.037 | 0.031 | 0.03 |
| HCV 3-1 | 2.634 | 2.721 | 2.882 | 2.667 | 2.369 | 1.972 |
| HCV 3-5 | 0.031 | 1.330 | 2.183 | 1.094 | 0.043 | 0.316 |
| HCV 3-13 | 0.142 | 1.957 | 2.592 | 2.490 | 0.668 | 0.683 |
| HCV 3-14 | 0.048 | 1.785 | 2.784 | 0.225 | 0.082 | 0.673 |
| HCV 3-16 | 0.022 | 2.189 | 2.305 | 0.194 | 0.409 | 0.862 |
| HCV 3-17 | 0.132 | 2.476 | 2.758 | 1.148 | 0.124 | 1.718 |
| HCV 3-19 | 0.022 | 1.804 | 2.289 | 0.337 | 0.050 | 0.529 |
| HCV 3-20 | 0.827 | 2.483 | 2.727 | 2.623 | 0.541 | 1.421 |
| HCV 3-21 | 0.043 | 1.415 | 2.594 | 2.599 | 2.011 | 1.885 |
| HCV 3-24 | 2.347 | 2.364 | 2.807 | 2.387 | 1.857 | 2.281 |
| HCV 3-25 | 1.429 | 2.369 | 2.515 | 2.136 | 0.162 | 0.528 |
| HCV 3-28 | 2.633 | 2.526 | 2.493 | 2.800 | 0.358 | 0.927 |
| HCV 3-29 | 0.748 | 2.276 | 2.535 | 2.600 | 0.233 | 1.028 |
| HCV 3-30 | 1.061 | 2.427 | 2.484 | 2.791 | 1.356 | 1.584 |
| HCV 3-34 | 0.014 | 1.490 | 1.562 | 0.714 | 0.057 | 0.373 |
| HCV 3-38 | 1.978 | 2.428 | 2.156 | 2.351 | 1.398 | 1.524 |
| HCV 3-39 | 2.201 | 2.367 | 2.425 | 1.974 | 0.130 | 0.842 |
| HCV 3-40 | 2.746 | 2.735 | 2.805 | 2.512 | 1.495 | 2.172 |
| HCV 3-41 | 2.679 | 2.512 | 2.885 | 2.637 | 1.468 | 1.864 |

*The values given are absorbances at 492 nm. "—" indicates the sample was not tested.

EXAMPLE 5

Branched Hybrid and Cluster Peptides

The immunoreactivity of branched peptides 3KH8, C6C, 3KC10C and C11 (Table 1) were tested on panel 3 containing 41 known HCV-reactive samples using the ELISA assay format as described in Example 1. Table 6 shows the results for these peptides. Peptide 3KH8 is from the HCV core protein, C6C and C11 are from the NS-5 protein, and 3KC10C is from the NS-4 and core proteins. Each sample (except 6 and 10) was reactive with one or more of the branched peptides.

TABLE 6

| Sample | 3KC10C Abs.[a] | 3KH8 Abs. | C6C Abs. | C11 Abs. |
|---|---|---|---|---|
| Blank | 0.056 | 0.053 | 0.054 | 0.056 |
| NRC | 0.024 | 0.018 | 0.022 | 0.193 |
| HCV Panel 3 | | | | |
| 1 | over | 1.842 | 1.629 | 2.550 |
| 2 | 0.039 | 0.813 | 0.036 | 0.111 |
| 3 | 1.747 | 0.659 | 0.042 | 0.146 |
| 4 | 2.438 | 0.250 | 0.017 | 0.181 |
| 5 | 2.453 | 2.219 | 2.366 | 2.572 |
| 6 | 0.030 | 0.133 | 0.046 | 0.184 |
| 7 | 2.499 | 0.890 | 1.262 | 1.906 |
| 8 | 1.051 | 0.863 | 0.021 | 0.334 |
| 9 | 2.677 | 0.801 | 0.051 | 0.184 |
| 10 | 0.013 | 0.050 | 0.018 | 0.052 |
| 11 | 2.340 | 1.998 | 1.404 | 2.359 |
| 12 | 0.625 | 0.153 | 0.026 | 0.065 |
| 13 | 2.092 | 2.495 | 0.933 | 1.392 |
| 14 | 1.940 | 1.893 | 2.317 | 2.342 |
| 15 | 0.676 | 0.202 | 0.057 | 0.165 |
| 16 | 1.266 | 2.642 | 2.478 | 2.671 |
| 17 | 1.258 | 2.595 | over | over |
| 18 | 2.609 | 0.883 | 0.050 | 0.824 |
| 19 | 2.176 | 2.901 | 1.704 | 2.556 |
| 20 | over | 2.678 | 0.208 | 1.439 |
| 21 | 0.178 | 2.127 | over | 2.574 |
| 22 | 0.424 | 0.137 | 0.044 | 0.115 |
| 23 | 1.222 | 0.879 | 0.122 | 0.261 |
| 24 | 2.426 | 2.420 | 0.361 | 0.835 |
| 25 | 2.472 | 1.975 | 2.008 | 2.442 |
| 26 | 2.558 | 1.256 | 1.586 | 2.233 |
| 27 | 2.234 | 1.455 | 2.473 | 2.359 |
| 28 | 1.931 | 2.503 | 2.879 | 2.706 |
| 29 | 2.152 | 2.003 | 0.258 | 1.143 |
| 30 | 1.100 | 2.797 | 0.083 | 0.259 |
| 31 | 2.264 | 0.589 | 0.075 | 0.250 |
| 32 | 0.869 | 1.683 | 0.046 | 0.080 |
| 33 | 2.033 | 2.118 | 2.591 | 2.317 |
| 34 | 2.366 | 1.737 | 0.125 | 2.631 |
| 35 | 0.117 | 0.155 | 0.054 | 0.239 |
| 36 | 1.961 | 2.281 | 2.347 | 2.353 |
| 37 | 0.031 | 0.121 | 0.060 | 0.113 |
| 38 | 2.287 | 2.252 | 1.404 | 1.715 |
| 39 | 1.346 | 1.292 | 0.551 | 0.927 |
| 40 | 2.372 | 1.943 | 2.336 | 2.585 |
| 41 | 2.455 | 2.366 | 2.813 | 2.480 |

[a]Absorbances are at 492 nm

EXAMPLE 6

Formulation Study and Detection of NANBH-Associated Antibodies Using a Mixture of Peptides A mixture of peptides 3KC10C, 3KH8, C11 and C12 was coated on wells of 96-well plates and assayed for HCV antibodies using the ELISA procedure described in Example 1. The sequence of each peptide is provided in Table 1 and the formulations are shown in Table 7. The results from three of these formulations (1, 7 and 8) are reported in Table 8. The most sensitive formulation was obtained at a weight ratio of 1:2:1:3 for 3KC10C:3KH8:C11:C12.

TABLE 7

| Formula | Wt. Ratio[a] |
|---|---|
| 1 | 1.5:2:1:3 |
| 2 | 1.5:3:2:3 |
| 3 | 2:2:1:3 |
| 4 | 2:2:2:3 |
| 5 | 2:3:2:3 |
| 6 | 2:3:1:3 |
| 7 | 1:2:1:3 |
| 8 | 1.5:2:0.5:3 |
| 9 | 1.5:3:0.5:3 |
| 10 | 1.5:3:1:3 |
| 11 | 1.5:2:1:5 |
| 12 | 1.5:2:0.5:5 |

[a]Peptides 3KC10C:3KH8:C11:C12

TABLE 8

| Sample | Formula #1 Abs | Formula #1 Ratio | Formula #7 Abs | Formula #7 Ratio | Formula #8 Abs | Formula #8 Ratio |
|---|---|---|---|---|---|---|
| NRC | 0.030 | 0.41 | 0.062 | 0.64 | 0.043 | 0.41 |
| WRC | 0.180 | 2.46 | 0.212 | 2.20 | 0.260 | 2.49 |
| SRC | 0.487 | 6.67 | 0.643 | 6.67 | 0.695 | 6.67 |
| Cutoff | 0.073 | | 0.096 | | 0.104 | |
| HCV 3-03 | 2.809 | 38.45 | 2.361 | 24.48 | 2.359 | 22.63 |
| HCV 3-08 | 1.052 | 14.40 | 1.223 | 12.86 | 1.226 | 11.76 |
| HCV 3-12 | 0.882 | 12.07 | 0.969 | 10.05 | 1.026 | 9.84 |
| HCV 3-15 | 0.463 | 6.34 | 0.512 | 5.31 | 0.796 | 7.64 |
| HCV 3-21 | 2.783 | 38.10 | 2.388 | 24.76 | 2.825 | 27.10 |
| HCV 3-22 | 0.571 | 7.82 | 0.661 | 6.85 | 0.637 | 6.11 |
| HCV 3-23 | 1.660 | 22.72 | 1.947 | 20.19 | 1.909 | 18.31 |
| HCV 3-32 | 1.798 | 24.61 | 2.274 | 23.58 | 2.015 | 19.33 |
| HCV 3-35 | 0.144 | 1.97 | 0.244 | 2.53 | 0.185 | 1.77 |
| HCV 3-37 | 0.942 | 12.90 | 1.419 | 14.71 | 1.168 | 11.20 |
| UBI-01 | 0.524 | 7.17 | 0.776 | 8.05 | 0.485 | 4.65 |
| UBI-03 | 0.145 | 1.98 | 0.192 | 1.99 | 0.206 | 1.98 |
| UBI-04 | 0.309 | 4.23 | 0.385 | 3.99 | 0.445 | 4.27 |
| UBI-05 | 0.104 | 1.42 | 0.234 | 2.43 | 0.133 | 1.28 |
| UBI-06 | 0.169 | 2.31 | 0.230 | 2.38 | 0.248 | 2.38 |
| UBI-07 | 0.489 | 6.69 | 0.570 | 5.91 | 0.616 | 5.91 |
| UBI-11 | 0.450 | 6.16 | 0.635 | 6.58 | 0.408 | 3.91 |

---

We claim:

1. A peptide composition comprising at least one linear or branched peptide represented by the formula (peptide)—Y (peptide)$_2$X (peptide)$_4$X$_2$X (peptide)$_8$X$_4$X$_2$X (peptide)$_{16}$X$_8$X$_4$X$_2$X wherein (peptide) is a peptide moiety, Y is an OH or NH$_2$ group on the carbonyl group of the C terminal amino acid of said peptide moiety, X is an amino acid or an amino acid analog having two amino groups and one carboxyl group, each group capable of forming a peptide bond linkage, and said peptide moiety is specifically immunoreactive with HCV antibodies, wherein said peptide moiety consists of an amino acid sequence of all of or a segment of at least 60 amino acids of L1C or L2C, wherein L1C and L2C have the amino acid sequences, respectively, of SEQ ID NO:6 and SEQ ID NO:11, or of a sequence from a corresponding region in a strain or isolate of HCV.

2. The peptide composition of claim 1 comprising a mixture of two or more of said peptides.

3. The peptide composition of claim 1, wherein said peptide is conjugated to a carrier.

4. The peptide composition of claim 1 wherein said peptide moiety further comprises a segment of one of said sequences.

5. The peptide composition of claim 1 wherein said peptide is linear.

6. The peptide composition of claim 5 wherein said sequence is the sequence designated as L1C.

7. The peptide composition of claim 6 wherein said peptide is L1A, L1B, L1C, 3KL1C, L4A, L4B, L4C, 3KL4C, C12, C13 or C14A.

8. The peptide composition of claim 5, wherein said sequence is the sequence designated as L2C.

9. The peptide composition of claim 8 wherein said peptide is L2A, L2B, L2C, L3A, L3B or L3C.

10. The peptide composition of claim 1, wherein said peptide is a branched dimer.

11. The peptide composition of claim 10, wherein said peptide is 3KC14B.

12. A peptide composition comprising a peptide selected from a group consisting of peptides L1C, 3KL1C, L2C, L3A, 3KL4C, and C12.

13. A peptide composition comprising peptides 3KC10C, C11, C12 and 3KH8.

14. An isolated linear or branched peptide of about 60 amino acids comprising a sequence of amino acids 20 to 77 of SEQ ID NO:6, a sequence of amino acids 20 to 77 of SEQ ID NO:11, or an analog thereof having a sequence from a corresponding region of a strain or isolate of HCV, wherein said peptide is specifically immunoreactive with HCV antibodies.

15. An isolated linear or branched peptide, wherein said peptide is about 70 amino acids and said amino acid sequence is of amino acids 11 to 81 of SEQ ID NO:6 or SEQ ID NO:11.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "NORVALINE"

( i x ) FEATURE:
        ( A ) NAME/KEY: Modified-site
        ( B ) LOCATION: 7
        ( D ) OTHER INFORMATION: /note= "NORVALINE"

( x i ) SEQUENCE DESCRIPTION: SEQ ID NO:1:

```
Lys Ala Xaa Pro Leu Glu Xaa Val Lys Gly Gly Arg His Leu Ile Phe
 1               5                  10                  15

Cys His Ser Lys Lys Lys Cys Asp Glu Leu Ala Ala Lys Leu Val Ala
            20                  25                  30
```

5,639,594

23

24

-continued

| Leu | Gly | Ile | Asn | Ala | Val | Ala | Tyr | Tyr | Arg | Gly | Leu | Asp | Val | Ser | Val |
|     |     | 35  |     |     |     |     | 40  |     |     |     |     | 45  |     |     |     |

| Ile | Pro | Thr | Ser | Gly | Asp | Val | Val | Val | Ala | Thr | Asp | Ala | Leu | Met |
|     |     | 50  |     |     |     |     | 55  |     |     |     |     | 60  |     |     |     |

| Thr | Gly | Tyr | Thr | Gly | Asp | Phe | Asp | Ser | Val | Ile | Asp | Cys | Asn | Thr | Cys |
| 65  |     |     |     |     | 70  |     |     |     |     | 75  |     |     |     |     | 80  |

Val ( 2 ) INFORMATION FOR SEQ ID NO:2:

( i ) SEQUENCE CHARACTERISTICS:
        ( A ) LENGTH: 71 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "NORVALINE"

( x i ) SEQUENCE DESCRIPTION: SEQ ID NO:2:

| Gly | Arg | His | Leu | Ile | Xaa | Cys | His | Thr | Lys | Lys | Lys | Cys | Asp | Glu | Leu |
| 1   |     |     |     | 5   |     |     |     |     | 10  |     |     |     |     | 15  |     |

| Ala | Ala | Lys | Leu | Val | Ala | Leu | Gly | Ile | Asn | Ala | Val | Ala | Tyr | Tyr | Arg |
|     |     |     | 20  |     |     |     |     |     | 25  |     |     |     |     | 30  |     |

| Gly | Leu | Asp | Val | Ser | Val | Ile | Pro | Thr | Ser | Gly | Asp | Val | Val | Val | Val |
|     |     | 35  |     |     |     |     | 40  |     |     |     |     | 45  |     |     |     |

| Ala | Thr | Asp | Ala | Leu | Met | Thr | Gly | Tyr | Thr | Gly | Asp | Phe | Asp | Ser | Val |
|     | 50  |     |     |     |     | 55  |     |     |     |     | 60  |     |     |     |     |

| Ile | Asp | Cys | Asn | Thr | Cys | Val |
| 65  |     |     |     |     | 70  |     |

( 2 ) INFORMATION FOR SEQ ID NO:3:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "NORVALINE"

( i x ) FEATURE:
        ( A ) NAME/KEY: Modified-site
        ( B ) LOCATION: 7
        ( D ) OTHER INFORMATION: /note= "NORVALINE"

( i x ) FEATURE:
        ( A ) NAME/KEY: Modified-site
        ( B ) LOCATION: 16
        ( D ) OTHER INFORMATION: /note= "NORVALINE"

( i x ) FEATURE:
        ( A ) NAME/KEY: Modified-site
        ( B ) LOCATION: 26
        ( D ) OTHER INFORMATION: /note= "NORLEUCINE"

( i x ) FEATURE:
        ( A ) NAME/KEY: Modified-site
        ( B ) LOCATION: 31
        ( D ) OTHER INFORMATION: /note= "NORVALINE"

( i x ) FEATURE:
    ( A ) NAME/KEY: Modified-site
    ( B ) LOCATION: 38
    ( D ) OTHER INFORMATION: /note= "NORVALINE"

( i x ) FEATURE:
    ( A ) NAME/KEY: Modified-site
    ( B ) LOCATION: 46
    ( D ) OTHER INFORMATION: /note= "NORVALINE"

( i x ) FEATURE:
    ( A ) NAME/KEY: Modified-site
    ( B ) LOCATION: 57
    ( D ) OTHER INFORMATION: /note= "NORVALINE"

( i x ) FEATURE:
    ( A ) NAME/KEY: Modified-site
    ( B ) LOCATION: 63
    ( D ) OTHER INFORMATION: /note= "NORLEUCINE"

( i x ) FEATURE:
    ( A ) NAME/KEY: Modified-site
    ( B ) LOCATION: 74
    ( D ) OTHER INFORMATION: /note= "NORVALINE"

( x i ) SEQUENCE DESCRIPTION: SEQ ID NO:3:

```
Lys  Ala  Xaa  Pro  Leu  Glu  Xaa  Val  Lys  Gly  Gly  Arg  His  Leu  Ile  Xaa
 1                  5                        10                       15

Cys  His  Thr  Lys  Lys  Lys  Cys  Asp  Glu  Xaa  Ala  Ala  Lys  Leu  Xaa  Ala
              20                        25                       30

Leu  Gly  Ile  Asn  Ala  Xaa  Ala  Tyr  Tyr  Arg  Gly  Leu  Asp  Xaa  Ser  Val
         35                        40                       45

Ile  Pro  Thr  Ser  Gly  Glu  Val  Val  Xaa  Val  Ala  Thr  Asp  Ala  Xaa  Met
    50                       55                       60

Thr  Gly  Tyr  Thr  Gly  Glu  Phe  Asp  Ser  Xaa  Ile  Asp  Cys  Asn  Thr  Cys
65                      70                      75                       80

Val
```

( 2 ) INFORMATION FOR SEQ ID NO:4:

( i ) SEQUENCE CHARACTERISTICS:
        ( A ) LENGTH: 62 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Lys  Lys  Lys  Cys  Asp  Glu  Leu  Ala  Ala  Lys  Leu  Val  Ala  Leu  Gly  Ile
 1                  5                        10                       15

Asn  Ala  Val  Ala  Tyr  Tyr  Arg  Gly  Leu  Asp  Val  Ser  Val  Ile  Pro  Thr
              20                        25                       30

Ser  Gly  Asp  Val  Val  Val  Val  Ala  Thr  Asp  Ala  Leu  Met  Thr  Gly  Tyr
         35                        40                       45

Thr  Gly  Asp  Phe  Asp  Ser  Val  Ile  Asp  Cys  Asn  Thr  Cys  Val
    50                       55                       60
```

( 2 ) INFORMATION FOR SEQ ID NO:5:

( i ) SEQUENCE CHARACTERISTICS:
        ( A ) LENGTH: 71 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
      Gly  Arg  His  Leu  Ile  Phe  Cys  His  Ser  Lys  Lys  Cys  Asp  Glu  Leu
      1              5                        10                       15

Ala  Ala  Lys  Leu  Val  Ala  Leu  Gly  Ile  Asn  Ala  Val  Ala  Tyr  Tyr  Arg
                     20                       25                       30

Gly  Leu  Asp  Val  Ser  Val  Ile  Pro  Thr  Ser  Gly  Asp  Val  Val  Val  Val
                     35                       40                       45

Ala  Thr  Asp  Ala  Leu  Met  Thr  Gly  Tyr  Thr  Gly  Asp  Phe  Asp  Ser  Val
                50                       55                       60

Ile  Asp  Cys  Asn  Thr  Cys  Val
      65                       70
```

( 2 ) INFORMATION FOR SEQ ID NO:6:

( i ) SEQUENCE CHARACTERISTICS:
( A ) LENGTH: 81 amino acids
( B ) TYPE: amino acid
( D ) TOPOLOGY: linear ( i i ) MOLECULE TYPE: peptide ( x i ) SEQUENCE DESCRIPTION: SEQ ID NO:6:

```
      Lys  Ala  Ile  Pro  Leu  Glu  Val  Ile  Lys  Gly  Gly  Arg  His  Leu  Ile  Phe
      1              5                        10                       15

Cys  His  Ser  Lys  Lys  Lys  Cys  Asp  Glu  Leu  Ala  Ala  Lys  Leu  Val  Ala
                     20                       25                       30

Leu  Gly  Ile  Asn  Ala  Val  Ala  Tyr  Tyr  Arg  Gly  Leu  Asp  Val  Ser  Val
                     35                       40                       45

Ile  Pro  Thr  Ser  Gly  Asp  Val  Val  Val  Ala  Thr  Asp  Ala  Leu  Met
                50                       55                       60

Thr  Gly  Tyr  Thr  Gly  Asp  Phe  Asp  Ser  Val  Ile  Asp  Cys  Asn  Thr  Cys
      65                       70                       75                       80

Val
```

( 2 ) INFORMATION FOR SEQ ID NO:7:

( i ) SEQUENCE CHARACTERISTICS:
( A ) LENGTH: 93 amino acids
( B ) TYPE: amino acid
( D ) TOPOLOGY: linear ( i i ) MOLECULE TYPE: peptide ( x i ) SEQUENCE DESCRIPTION: SEQ ID NO:7:

```
      Ala  Leu  Ser  Thr  Thr  Gly  Glu  Ile  Pro  Phe  Tyr  Gly  Lys  Ala  Ile  Pro
      1              5                        10                       15

Leu  Glu  Val  Ile  Lys  Gly  Gly  Arg  His  Leu  Ile  Phe  Cys  His  Ser  Lys
                     20                       25                       30

Lys  Lys  Cys  Asp  Glu  Leu  Ala  Ala  Lys  Leu  Val  Ala  Leu  Gly  Ile  Asn
                     35                       40                       45

Ala  Val  Ala  Tyr  Tyr  Arg  Gly  Leu  Asp  Val  Ser  Val  Ile  Pro  Thr  Ser
                50                       55                       60

Gly  Asp  Val  Val  Val  Ala  Thr  Asp  Ala  Leu  Met  Thr  Gly  Tyr  Thr
      65                       70                       75                       80

Gly  Asp  Phe  Asp  Ser  Val  Ile  Asp  Cys  Asn  Thr  Cys  Val
                     85                       90
```

( 2 ) INFORMATION FOR SEQ ID NO:8:

( i ) SEQUENCE CHARACTERISTICS:
       ( A ) LENGTH: 84 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:8:

```
Lys Lys Lys Lys Ala Ile Pro Leu Glu Val Ile Lys Gly Gly Arg His
1               5                   10                  15
Leu Ile Phe Cys His Ser Lys Lys Lys Cys Asp Glu Leu Ala Ala Lys
            20                  25                  30
Leu Val Ala Leu Gly Ile Asn Ala Val Ala Tyr Tyr Arg Gly Leu Asp
        35                  40                  45
Val Ser Val Ile Pro Thr Ser Gly Asp Val Val Val Ala Thr Asp
    50                  55                  60
Ala Leu Met Thr Gly Tyr Thr Gly Asp Phe Asp Ser Val Ile Asp Cys
65                  70                  75                  80
Asn Thr Cys Val
```

( 2 ) INFORMATION FOR SEQ ID NO:9:

( i ) SEQUENCE CHARACTERISTICS:
       ( A ) LENGTH: 62 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:9:

```
Lys Lys Lys Cys Asp Glu Leu Ala Ala Ala Leu Arg Gly Met Gly Val
1               5                   10                  15
Asn Ala Val Ala Tyr Tyr Arg Gly Leu Asp Val Ser Val Ile Pro Thr
            20                  25                  30
Gln Gly Asp Val Val Val Val Ala Thr Asp Ala Leu Met Thr Gly Tyr
        35                  40                  45
Thr Gly Asp Phe Asp Ser Val Ile Asp Cys Asn Val Ala Val
    50                  55                  60
```

( 2 ) INFORMATION FOR SEQ ID NO:10:

( i ) SEQUENCE CHARACTERISTICS:
       ( A ) LENGTH: 71 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:10:

```
Gly Arg His Leu Ile Phe Cys His Ser Lys Lys Cys Asp Glu Leu
1               5                   10                  15
Ala Ala Ala Leu Arg Gly Met Gly Val Asn Ala Val Ala Tyr Tyr Arg
            20                  25                  30
Gly Leu Asp Val Ser Val Ile Pro Thr Gln Gly Asp Val Val Val Val
        35                  40                  45
Ala Thr Asp Ala Leu Met Thr Gly Tyr Thr Gly Asp Phe Asp Ser Val
    50                  55                  60
Ile Asp Cys Asn Val Ala Val
65                  70
```

( 2 ) INFORMATION FOR SEQ ID NO:11:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Lys Ala Ile Pro Leu Ala Phe Ile Lys Gly Gly Arg His Leu Ile Phe
1               5                   10                  15
Cys His Ser Lys Lys Cys Asp Glu Leu Ala Ala Ala Leu Arg Gly
            20              25                  30
Met Gly Val Asn Ala Val Ala Tyr Tyr Arg Gly Leu Asp Val Ser Val
            35              40                  45
Ile Pro Thr Gln Gly Asp Val Val Val Ala Thr Asp Ala Leu Met
    50              55                  60
Thr Gly Tyr Thr Gly Asp Phe Asp Ser Val Ile Asp Cys Asn Val Ala
65                  70                  75                  80
Val
```

( 2 ) INFORMATION FOR SEQ ID NO:12:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Ala Leu Gly His Glu Gly Glu Ile Pro Phe Tyr Gly Lys Ala Ile Pro
1               5                   10                  15
Leu Ala Phe Ile Lys Gly Gly Arg His Leu Ile Phe Cys His Ser Lys
            20              25                  30
Lys Lys Cys Asp Glu Leu Ala Ala Ala Leu Arg Gly Met Gly Val Asn
            35              40                  45
Ala Val Ala Tyr Tyr Arg Gly Leu Asp Val Ser Val Ile Pro Thr Gln
        50              55                  60
Gly Asp Val Val Val Val Ala Thr Asp Ala Leu Met Thr Gly Tyr Thr
65                  70                  75                  80
Gly Asp Phe Asp Ser Val Ile Asp Cys Asn Val Ala Val
                85                  90
```

( 2 ) INFORMATION FOR SEQ ID NO:13:

( i ) SEQUENCE CHARACTERISTICS:
        ( A ) LENGTH: 62 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Lys Lys Lys Cys Asp Glu Leu Ala Ala Ala Leu Arg Gly Met Gly Val
1               5                   10                  15
Asn Ala Val Ala Tyr Tyr Arg Gly Leu Asp Val Ser Val Ile Pro Thr
            20              25                  30
Gln Gly Asp Val Val Val Val Ala Thr Asp Ala Leu Met Thr Gly Tyr
            35              40                  45
```

```
          Thr   Gly   Asp   Phe   Asp   Ser   Val   Ile   Asp   Cys   Asn   Val   Cys   Val
                50                      55                      60
```

(2) INFORMATION FOR SEQ ID NO:14:

(i) SEQUENCE CHARACTERISTICS:
        (A) LENGTH: 71 amino acids
        (B) TYPE: amino acid
        (D) TOPOLOGY: linear (ii) MOLECULE TYPE: peptide (xi) SEQUENCE DESCRIPTION: SEQ ID NO:14:

```
   Gly   Arg   His   Leu   Ile   Phe   Cys   His   Ser   Lys   Lys   Cys   Asp   Glu   Leu
   1                       5                             10                      15

Ala   Ala   Ala   Leu   Arg   Gly   Met   Gly   Val   Asn   Ala   Val   Ala   Tyr   Tyr   Arg
                     20                            25                            30

Gly   Leu   Asp   Val   Ser   Val   Ile   Pro   Thr   Gln   Gly   Asp   Val   Val   Val
                     35                            40                            45

Ala   Thr   Asp   Ala   Leu   Met   Thr   Gly   Tyr   Thr   Gly   Asp   Phe   Asp   Ser   Val
                     50                            55                            60

Ile   Asp   Cys   Asn   Val   Cys   Val
   65                      70
```

(2) INFORMATION FOR SEQ ID NO:15:

(i) SEQUENCE CHARACTERISTICS:
        (A) LENGTH: 81 amino acids
        (B) TYPE: amino acid
        (D) TOPOLOGY: linear (ii) MOLECULE TYPE: peptide (xi) SEQUENCE DESCRIPTION: SEQ ID NO:15:

```
   Lys   Ala   Ile   Pro   Leu   Ala   Phe   Ile   Lys   Gly   Gly   Arg   His   Leu   Ile   Phe
   1                       5                             10                            15

Cys   His   Ser   Lys   Lys   Cys   Asp   Glu   Leu   Ala   Ala   Ala   Leu   Arg   Gly
                     20                            25                            30

Met   Gly   Val   Asn   Ala   Val   Ala   Tyr   Tyr   Arg   Gly   Leu   Asp   Val   Ser   Val
                     35                            40                            45

Ile   Pro   Thr   Gln   Gly   Asp   Val   Val   Val   Ala   Thr   Asp   Ala   Leu   Met
         50                            55                            60

Thr   Gly   Tyr   Thr   Gly   Asp   Phe   Asp   Ser   Val   Ile   Asp   Cys   Asn   Val   Cys
   65                            70                            75                            80

Val
```

(2) INFORMATION FOR SEQ ID NO:16:

(i) SEQUENCE CHARACTERISTICS:
        (A) LENGTH: 53 amino acids
        (B) TYPE: amino acid
        (D) TOPOLOGY: linear (ii) MOLECULE TYPE: peptide (xi) SEQUENCE DESCRIPTION: SEQ ID NO:16:

```
   Lys   Lys   Lys   Cys   Asp   Glu   Leu   Ala   Ala   Lys   Leu   Val   Ala   Leu   Gly   Ile
   1                       5                             10                            15

Asn   Ala   Val   Ala   Tyr   Tyr   Lys   Gly   Leu   Asp   Val   Ser   Val   Ile   Pro   Thr
                     20                            25                            30

Ser   Gly   Asp   Thr   Asp   Ala   Leu   Met   Thr   Gly   Tyr   Thr   Gly   Asp   Phe   Asp
                     35                            40                            45
```

```
            Ser  Val  Ile  Asp  Cys
                           50
```

( 2 ) INFORMATION FOR SEQ ID NO:17:

( i ) SEQUENCE CHARACTERISTICS:
    ( A ) LENGTH: 62 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

```
  Gly  Lys  His  Leu  Ile  Phe  Cys  His  Ser  Lys  Lys  Cys  Asp  Glu  Leu
  1              5                        10                       15

Ala  Ala  Lys  Leu  Val  Ala  Leu  Gly  Ile  Asn  Ala  Val  Ala  Tyr  Tyr  Lys
                 20                       25                       30

Gly  Leu  Asp  Val  Ser  Val  Ile  Pro  Thr  Ser  Gly  Asp  Thr  Asp  Ala  Leu
            35                            40                       45

Met  Thr  Gly  Tyr  Thr  Gly  Asp  Phe  Asp  Ser  Val  Ile  Asp  Cys
       50                      55                            60
```

( 2 ) INFORMATION FOR SEQ ID NO:18:

( i ) SEQUENCE CHARACTERISTICS:
    ( A ) LENGTH: 72 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:18:

```
  Lys  Ala  Ile  Pro  Leu  Glu  Val  Ile  Lys  Gly  Gly  Lys  His  Leu  Ile  Phe
  1              5                        10                       15

Cys  His  Ser  Lys  Lys  Cys  Asp  Glu  Leu  Ala  Ala  Lys  Leu  Val  Ala
                 20                       25                       30

Leu  Gly  Ile  Asn  Ala  Val  Ala  Tyr  Tyr  Lys  Gly  Leu  Asp  Val  Ser  Val
            35                            40                       45

Ile  Pro  Thr  Ser  Gly  Asp  Thr  Asp  Ala  Leu  Met  Thr  Gly  Tyr  Thr  Gly
       50                      55                            60

Asp  Phe  Asp  Ser  Val  Ile  Asp  Cys
  65                       70
```

( 2 ) INFORMATION FOR SEQ ID NO:19:

( i ) SEQUENCE CHARACTERISTICS:
    ( A ) LENGTH: 75 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:19:

```
  Lys  Lys  Lys  Lys  Ala  Ile  Pro  Leu  Glu  Val  Ile  Lys  Gly  Gly  Lys  His
  1              5                        10                       15

Leu  Ile  Phe  Cys  His  Ser  Lys  Lys  Cys  Asp  Glu  Leu  Ala  Ala  Lys
                 20                       25                       30

Leu  Val  Ala  Leu  Gly  Ile  Asn  Ala  Val  Ala  Tyr  Tyr  Lys  Gly  Leu  Asp
            35                            40                       45

Val  Ser  Val  Ile  Pro  Thr  Ser  Gly  Asp  Thr  Asp  Ala  Leu  Met  Thr  Gly
       50                      55                            60

Tyr  Thr  Gly  Asp  Phe  Asp  Ser  Val  Ile  Asp  Cys
  65                       70                       75
```

5,639,594

37

-continued ( 2 ) INFORMATION FOR SEQ ID NO:20:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Glu  Ile  Leu  Arg  Lys  Ser  Arg  Arg  Phe  Ala  Gln  Ala  Leu  Pro  Val  Trp
 1                    5                        10                       15

Ala  Arg  Pro  Asp  Tyr  Asn  Pro  Pro  Leu  Val  Glu  Thr  Trp  Lys  Lys  Pro
              20                        25                       30

Asp  Tyr  Glu  Pro  Pro  Val  Val  His  Gly  Cys  Pro  Leu  Pro  Pro  Pro  Lys
         35                        40                       45

Ser  Pro  Pro  Val  Pro  Pro  Pro  Arg  Lys  Lys  Arg  Thr
     50                        55                       60
```

( 2 ) INFORMATION FOR SEQ ID NO:21:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Glu  Ile  Pro  Phe  Tyr  Gly  Lys  Ala  Ile  Pro  Leu  Glu  Val  Ile  Lys  Gly
 1                    5                        10                       15

Gly  Arg  His  Leu  Ile  Phe  Cys  His  Ser  Lys  Lys  Lys  Cys  Asp  Glu  Leu
              20                        25                       30

Ala  Ala  Lys  Leu  Val  Ala  Leu
         35
```

( 2 ) INFORMATION FOR SEQ ID NO:22:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Ser  Gly  Lys  Pro  Ala  Ile  Ile  Pro  Asp  Arg  Glu  Val  Leu  Tyr  Arg  Glu
 1                    5                        10                       15

Phe  Asp  Glu  Met  Glu  Glu  Cys  Ser  Gln  His  Leu  Pro  Tyr  Ile  Glu  Gln
              20                        25                       30

Gly  Met  Met  Leu  Ala  Glu  Gln  Phe  Lys  Gln  Lys  Ala  Leu  Gly  Leu
         35                        40                       45
```

( 2 ) INFORMATION FOR SEQ ID NO:23:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

| Ser | Thr | Ile | Pro | Lys | Pro | Gln | Arg | Lys | Thr | Lys | Arg | Asn | Thr | Asn | Arg |
| 1 | | | | 5 | | | | | 10 | | | | | 15 | |
| Arg | Pro | Gln | Asp | Val | Lys | Phe | Pro | Gly | Gly | Gly | Gln | Ile | Val | Gly | Gly |
| | | | 20 | | | | | 25 | | | | | 30 | | |
| Val | Tyr | Leu | Leu | Pro | Arg | Arg | Gly | Pro | Arg | Leu | Gly | Val | Arg | Ala | Thr |
| | | 35 | | | | | 40 | | | | | 45 | | | |
| Arg | Lys | Thr | Ser | Glu | Arg | Ser | Gln | Pro | Arg | Gly | Arg | Arg | | | |
| | 50 | | | | | 55 | | | | | 60 | | | | |